(12) United States Patent
Russell

(10) Patent No.: US 6,892,086 B2
(45) Date of Patent: May 10, 2005

(54) MEDICAL ELECTRODE FOR PREVENTING THE PASSAGE OF HARMFUL CURRENT TO A PATIENT

(76) Inventor: Michael J. Russell, 715 Falcon, Davis, CA (US) 95616

( * ) Notice: Subject to any disclaimer, the term of this patent is extended or adjusted under 35 U.S.C. 154(b) by 110 days.

(21) Appl. No.: 09/982,320

(22) Filed: Oct. 17, 2001

(65) Prior Publication Data

US 2003/0013948 A1 Jan. 16, 2003

Related U.S. Application Data

(63) Continuation-in-part of application No. 09/903,778, filed on Jul. 11, 2001, now abandoned.

(51) Int. Cl.$^7$ ................................................ A61B 5/04
(52) U.S. Cl. ........................ 600/372; 600/382; 600/386; 327/328
(58) Field of Search ............................ 128/908; 606/32, 606/34, 41; 607/152; 600/372, 374, 378–379, 382, 386

(56) References Cited

U.S. PATENT DOCUMENTS

| | | | | |
|---|---|---|---|---|
| 3,603,811 | A | * 9/1971 | Day et al. ..................... | 327/328 |
| 3,605,728 | A | * 9/1971 | Ogle ............................ | 600/508 |
| 3,761,769 | A | * 9/1973 | Billin .......................... | 128/908 |
| 3,986,495 | A | * 10/1976 | Miller ......................... | 600/508 |
| 4,301,801 | A | 11/1981 | Schneiderman | |
| 4,303,073 | A | 12/1981 | Archibald | |
| 4,363,324 | A | 12/1982 | Kusserow | |
| 4,418,692 | A | 12/1983 | Guay | |
| 4,494,541 | A | 1/1985 | Archibald | |
| 4,520,818 | A | 6/1985 | Mickiewicz | |
| 4,548,207 | A | 10/1985 | Reimels | |
| 4,741,344 | A | * 5/1988 | Danby et al. ............... | 600/379 |
| 4,744,369 | A | * 5/1988 | Kroll .......................... | 600/509 |
| 4,898,169 | A | 2/1990 | Norman et al. | |
| 5,085,218 | A | * 2/1992 | Heil et al. .................... | 600/373 |
| 5,265,607 | A | * 11/1993 | Moberg ....................... | 600/383 |
| 5,433,732 | A | 7/1995 | Hirschberg et al. | |
| 5,498,242 | A | * 3/1996 | Cooke ......................... | 604/192 |
| 5,511,546 | A | * 4/1996 | Hon ............................ | 600/490 |
| 5,626,135 | A | * 5/1997 | Sanfilippo .................... | 600/391 |
| 5,761,019 | A | * 6/1998 | Kroll ........................... | 361/58 |
| 5,785,040 | A | * 7/1998 | Axelgaard .................... | 600/391 |
| 5,833,710 | A | * 11/1998 | Jacobson ....................... | 607/4 |
| 5,968,086 | A | * 10/1999 | Bonner et al. .............. | 607/122 |

OTHER PUBLICATIONS

Website printout of Medical Devices; Establishment of a Performance Standard for Electrode Lead Wires and Patient Cables.
Needle package insert from Nicolet Biomedical.
Pub Med Website printout.
Medtronic XOMED.
International Standard Printout.
Nicolet Biomedical 2000 Supplies Catalog.
5 copies of pictures of electrode male adaptor.
Asto–Med, Inc. Grass Instrument Divisions.

* cited by examiner

Primary Examiner—Roy D. Gibson
(74) Attorney, Agent, or Firm—DLA Piper Rudnick Gray Cary US LLP; Andrew V. Smith

(57) ABSTRACT

A medical electrode designed to prevent the passage of harmful electric current to a patient, thereby preventing tissue damage and electrocution. In the preferred embodiment, the inventive medical electrode is comprised of a proximal end, a distal end, a conductive lead connecting the proximal and distal ends, and a fuse located upon the medical electrode for preventing the passage of harmful electric current to a patient. For additional protection from induction current, the preferred location of the fuse is aft of the conductive lead element of the electrode. While a fuse is used in the preferred embodiment, the fuse could be replaced with a diode or a circuit breaker.

7 Claims, 6 Drawing Sheets

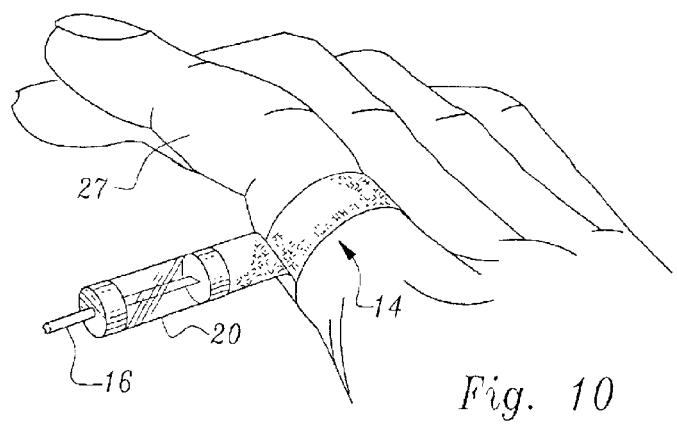
Fig. 10
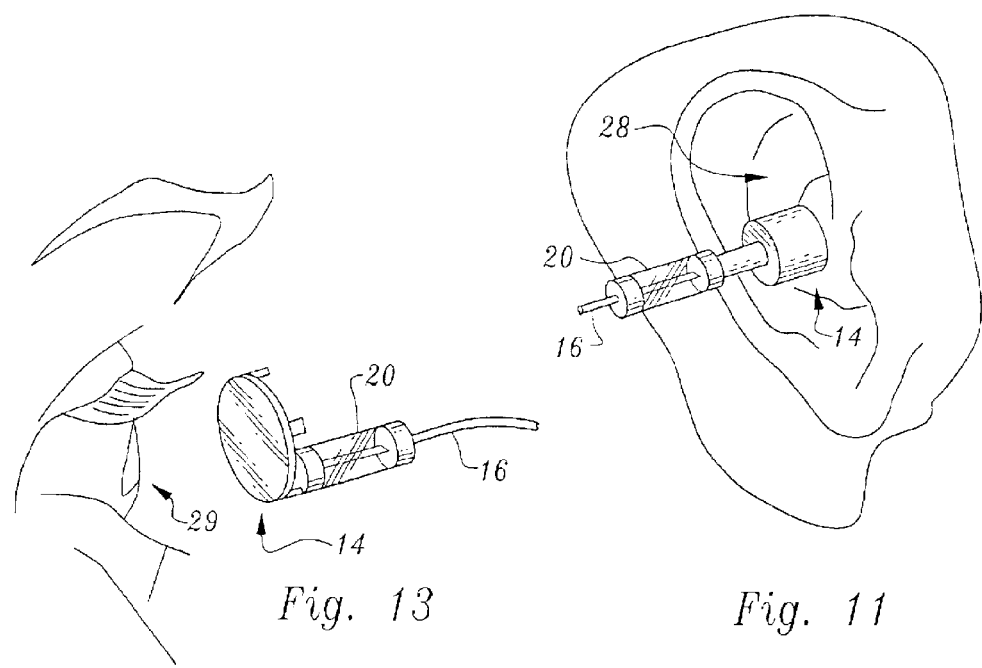
Fig. 13
Fig. 11
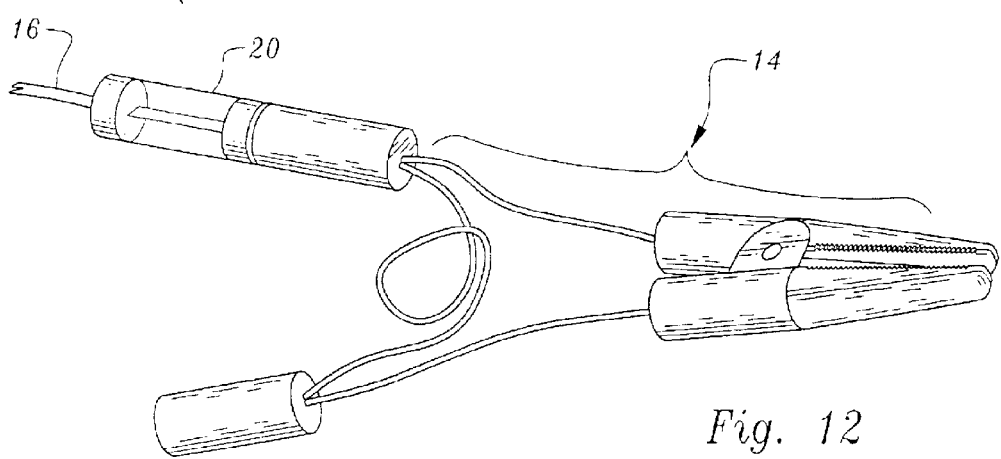
Fig. 12

MEDICAL ELECTRODE FOR PREVENTING THE PASSAGE OF HARMFUL CURRENT TO A PATIENT

CROSS REFERENCE TO RELATED APPLICATIONS

This is a continuation-in-part of U.S. patent application Ser. No. 09/903,778 filed on Jul. 11, 2001 abandoned.

TECHNICAL FIELD

This invention relates to medical electrodes, and more particularly, to preventing the passage of harmful electric current through a medical electrode attached to a patient.

BACKGROUND

Medical electrodes have been used for years to accomplish various clinical functions, including nerve stimulation, bio-feedback monitoring, electromyographs, and electroencephalograph (EEG) tests, to name a few. Medical electrodes are designed to either send electric current, from an electrical medical device to a living being, or else receive electric current generated by a living being. Medical electrodes can be used in both a human patient environment and in a veterinary environment.

Medical electrodes are generally comprised of a proximal end for coupling to a patient, a distal end for connecting to a medical appliance, such as an EEG machine, and an elongate wire lead located between the proximal and distal ends, for receiving or sending electrical current. Of these elements, the proximal end varies in structure according to the function necessary for a particular medical procedure. The different structural configurations of the proximal end of exemplary electrodes, include needle, plate, snap, and corkscrew electrodes, to name a few.

The passage of electrical current through a medical electrode is usually accomplished according to safe protocols, and generally does not result in any injury to a patient. However, it has been documented in a number of cases that the passage of current through a medical electrode connected to a patient has resulted in tissue burns, and even death by electrocution. The inventor has traced these unfortunate incidents back to five basic causes: 1) Equipment Failure; 2) Induction Current Phenomena; 3) Defective Machine and/or Defective Grounding of a Machine; 4) Constant DC current; and 5) Plugging an electrode having a male adaptor distal end directly into an AC power source.

The following actual case incidents, which are exemplary of each of the causes listed above, are being submitted here to further inform the reader of the problems with electrodes presently existing in the medical arts:

Case 1—Equipment Failure

An external stimulator hooked to a patient's ankle with medical electrodes was used with a computer averager to record somatosensory evoked potentials. The computer was wired so that it would drive the stimulator and record the averages of the potentials. During this case, an electro-cautery device was moved near a cord coupled to the external stimulator. The electro-cautery put out an inductive current that was strong enough to trigger the stimulator at a rate that was tied to the oscillating rate of the electro-cautery. This case lasted for eleven hours, at the end of which time, the stimulating platinum-iridium needle electrode tips were examined. It was found that enough heat had been generated such that the needles had vaporized and left a hole in the patient's ankle.

Case 2—Inductive Current Phenomena

A technician had encountered a minor problem with an electrode burn on a patient, which had occurred during feedback to an electro-cautery machine being used in an operating room, while performing a neuromonitoring procedure. The technician, being concerned about the possibility of this happening again, decided to disconnect the neuromonitoring equipment from the distal end of the electrodes, when she was not taking actual readings. However, the proximal ends of the electrodes remained connected to the patient. The technician coiled the disconnected electrode leads up, and taped them to a bed frame holding the patient, so that they would be out of the way, and available when she needed them again. A surgeon then used the electro-cautery equipment again, and this surgeon had a habit of pressing the "on" button of the electro-cautery probe when it was away from the patient. This particular electro-cautery probe used a very high voltage current and when the probe was turned on, away from the patient, the current took the path of least resistance into the coiled wires. The coiled wires acted as an induction coil receiver and further amplified the signal causing a significant burn on the patient.

Case 3—Defective Machine and/or Defective Grounding of a Machine

A neuromonitoring technician placed skin surface electrodes on a patient, but did not insure that the grounding impedances were low. The technician then recorded somatosensory evoked potentials for a back surgery. The electro-cautery being used in the surgery was faulty, and the neuromonitoring equipment allowed current to pass from the patient to the ground leads and caused burns upon the patient.

Case 4—Constant D.C. Current

An experienced engineer was testing equipment and placed a 1.5 volt D.C. battery in line with some equipment that he was testing on himself, while he had a pair of needle electrodes connected to his hand. The engineer became so focused on his work that he did not bother to remove the electrodes for over two hours. He did not notice that he was developing an electrolytic burn on this hand from the constant D.C. current, and now has a permanent scar.

Case 5—Plugging an Electrode Directly into an AC Power Source

In 1985, the first reported incidents of electrocution deaths from the exposed male connector pins of electrode lead wires being plugged into either AC power cords or wall outlets were recorded. Between 1985 and 1994, 24 infants or children received "macro-shock" (large externally applied currents) from medical electrodes, including five children who died by electrocution. These incidents were documented in the background section of the Apr. 28, 1997 final rule making for 21 CFR Part 898 entitled: "Medical Devices; Establishment of a Performance Standard for Electrode Lead Wires and Patient Cables" authored by the United States Food and Drug Administration (FDA).

The previous case examples demonstrate that medical electrode injuries and death can occur under a variety of real-world conditions. However, to date, the major focus with regard to medical electrode safety measures has been to deal with the electrocution problem, because this is the problem that can have the gravest consequences.

As noted in case 5, above, electrocution has resulted from the distal ends of medical electrodes, which have traditionally had male connector pins, being plugged into an AC power wall outlets. The solution, thus far, has been to change the distal end of medical electrodes to female connectors, thereby eliminating the male connector pins. Due to the fact that medical devices which couple to the electrodes still, by in large, require a male input, this problem has been solved by providing adaptors which couple a male pin back onto the female connector, which, in turn, is plugged into the medical device. These adaptors typically bear warning indicia such as "Warning: Do Not Use With AC Power Source or Apnea Monitors." However, these adaptors still convert the female connector end back to a male end, which despite such warnings, still present a real possibility of causing electrocution from plugging into a wall outlet.

Moreover, while the addition of adaptors present a better solution to the problem of electrocution from wall sockets, adaptors do not solve the problem of tissue burns and electrocution due to induction current phenomena. Induction current phenomena can be caused by RF leakage from defective medical devices such as an electro-cautery, or else can be cause from perfectly good devices, such as an MRI, which, by their nature produce significant amounts of electromagnetic energy. As noted in case 2, above, this induction current phenomena can occur when the electrode leads are uncoupled from a medical device, or an AC power source. So far, the answer to this inductance problem has been to post warnings on electrode packaging of the type shown on the packaging produced by Astro-Med, Inc., Grass Instrument Division of West Warwick, R.I. While package warnings certainly help keep medical personnel alert to the inductance problem, mere warnings are insufficient to stop tissue all tissue burns and electrocutions from occurring.

Various means have been devised for electrical medical appliances, in general, to prevent the passage of harmful current causing injuries or death. U.S. Pat. No. 5,433,732 (Hirschberg et al.) discloses an implantable heart defibrillator comprising a charging circuit located inside a housing with exterior electrodes for providing defibrillating current to a patient's heart. A complex current limiter is provided, exterior to the charging circuit, and in-line with the electrode wires. The current limiter prevents heart-damaging current from passing through to the electrode terminus. U.S. Pat. No. 4,418,692 (Guay) discloses an electro-cautery tip, which has a circuit breaker inside of the tip, for reducing the possibility of accidental activation of the device, which could damage tissue. Finally, the following patents disclose various electrical medical devices that have a fused component located in the circuitry of the device: U.S. Pat. No. 4,520,818 (Mickiewicz), U.S. Pat. No. 4,548,207 (Reimels), U.S. Pat. No. 4,363,324 (Kusserow), U.S. Pat. No. 4,494,541 (Archibald), U.S. Pat. No. 4,303,073 (Archibald), U.S. Pat. No. 4,301,801 (Schneiderman), U.S. Pat. No. 4,898,169 (Norman et al.).

While current stoppage means such as circuit breakers, current limiters, and fuses have been applied in the medical arts with regard to electrical medical devices, solutions for medical electrodes remain wanting. Many of the case histories noted previously involved electrical devices that had some type of built-in current stoppage means, yet harmful current was still passed to the electrodes to injure patients. Therefore, past solutions, have been inadequate to prevent the problem of burns and electrocution from harmful current passage through electrodes. Also, to this day, the international standards for medical electrical equipment (International Electrical Commission publication 60601-2-401) issue clear warnings regarding the danger of burns existing at the site of medical electrode input. These standards clearly show that as of yet, medical electrode design has not provided any closure to this burning problem.

Therefore, a need exists for a medical electrode that can both prevent injuries and death due to electrocution, from AC power sources and also injuries due to the inductance current phenomena.

The foregoing reflects the state of the art of which the inventor is aware, and is tendered with a view toward discharging the inventors' acknowledged duty of candor, which may be pertinent to the patentability of the present invention. It is respectfully stipulated, however, that the foregoing discussion does not teach or render obvious, singly or when considered in combination, the inventor's claimed invention.

SUMMARY OF THE INVENTION

The present invention is a medical electrode having a current stoppage means for preventing harmful electric current from passing to a patient. This stoppage means may be located at any point upon the electrode for purposes of preventing harmful levels of current passing from an AC power source to a patient. However, for additionally preventing induction current from passing to a patient, the preferred location of the current stoppage means is on the proximal end of the electrode, aft of the wire lead element of the electrode.

In the preferred embodiment, the current stoppage means is a fuse located upon the medical electrode, the fuse burning through when a certain harmful current passes into the fuse. However, the fuse could be replaced with a diode, a circuit breaker, or some other current stoppage means.

Accordingly, the following objects and advantages of the invention apply:

It is an object of this invention to provide a medical electrode that is safer than medical electrodes currently in existence.

It is an object of this invention to provide a medical electrode that can prevent the passage of harmful current to a patient.

It is another object of this invention to provide a medical electrode that is inexpensive to manufacture.

It is another object of this invention to provide a medical electrode that can prevent the passage of harmful current to a patient, wherein the harmful current originates from either an AC power source or an inductance current source.

Further objects and advantages of the invention will be brought out in the following portions of the specification, wherein the detailed description is for the purpose of fully disclosing preferred embodiments of the invention, without placing limitations thereon.

BRIEF DESCRIPTION OF THE DRAWINGS

The invention will be more fully understood by reference to the following drawings that are for illustrative purposes only:

FIG. 10 is a close-up perspective view of the inventive medical electrode, this embodiment being a strap electrode that is shown here wrapped around a patient's finger.

FIG. 11 is a close-up perspective view of the inventive medical electrode, this embodiment being an earplug electrode, shown inserted into a patient's ear canal.

FIG. 12 is a close-up perspective view of the inventive medical electrode, this embodiment being a clip electrode.

FIG. 13 is a close-up perspective view of the inventive medical electrode, this embodiment being a contact lens electrode.

DESCRIPTION OF THE PREFERRED EMBODIMENTS

The inventive medical electrode described herein stops the passage of harmful current to a patient. "Harmful current" as it is used here translates to current densities that are capable of causing tissue burns or even death by electrocution. Current density corresponds to the amount of current being applied to a square centimeter of tissue surface area. The International Electrotechnical Commission (IEC standard 60601-2-40) has established a current density of 2 mA r.m.s./cm$^2$ as a safety limit. Current densities beyond this safety limit tend to cause burns or electrocution.

Figure 1:
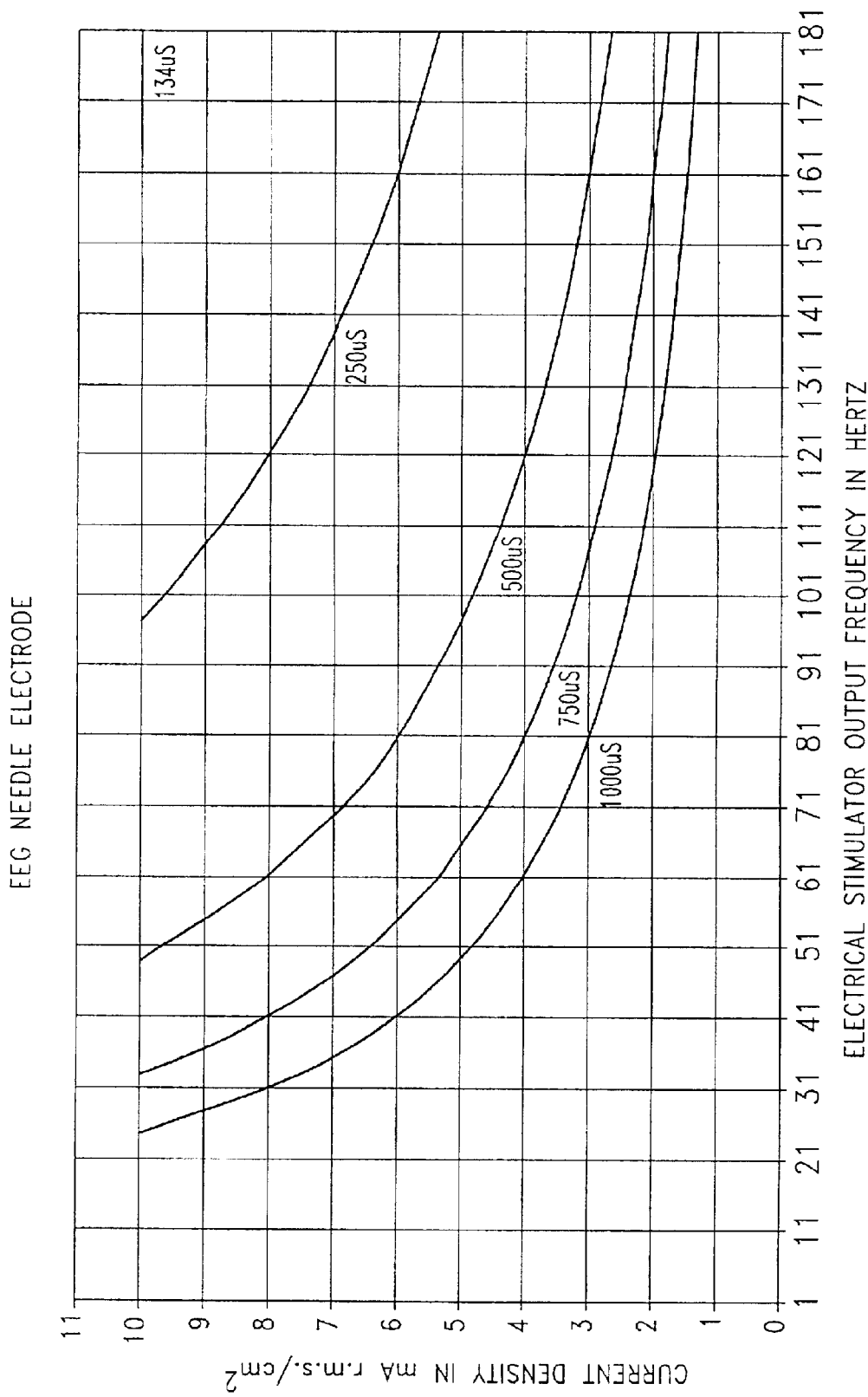
FIG. 1 is a graph of variables affecting current density for an EEG needle electrode.
Figure 2:
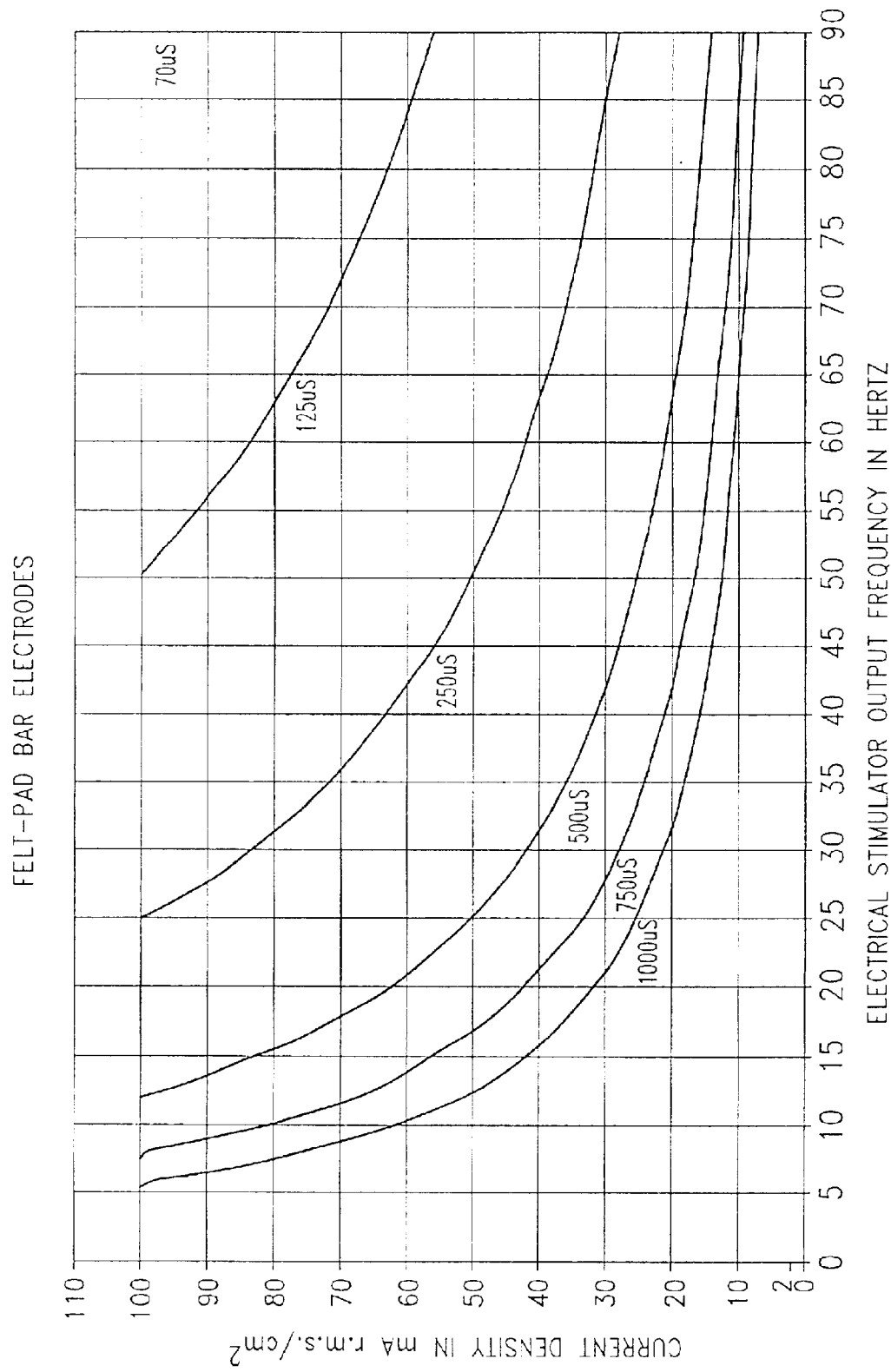
FIG. 2. is a graph of variables affecting current density for a felt pad bar electrode.

FIGS. 1 and 2 illustrate graphs showing the relationship of the variables of electrode surface area, time of applied current, and current frequency (in Hertz) on current density (mA r.m.s./cm$^2$). FIG. 1, is illustrative of a needle electrode, which has a small surface area, and FIG. 2 is for a felt-pad bar electrode having a large surface area. Each curve on the graphs is representative of current densities present at different times of applied current at different frequencies. Lengthier applications of current remain closer to the current density safety limit of 2 mA r.m.s./cm$^2$ for similar current frequency, than when compared to shorter applications. Also comparing the two graphs shows that the needle electrode, with its smaller surface area operates more closely to the safety limit at similar current frequencies than the felt pad bar electrode. These graphs also illustrate that while short applications of current at low frequencies are more likely to exceed the safety limit and cause burns, that even long applications of low frequencies can exceed the safety limit and cause burns. The variables of electrode surface area, time of applied current, and current frequency can be manipulated intentionally, or unintentionally such that a current density beyond 2 mA r.m.s./cm$^2$ can be reached rather easily in a hospital environment and cause burns.

Current sources of particular focus in a hospital environment include direct current (DC), alternating current (AC), and inductive current. Of these, AC and inductive current are most commonly present in a patient environment. AC results from power sources such as medical machinery, and from AC wall outlets. Inductive current results from stray RF leakage from electromagnetic machinery in perfectly good condition, such as nuclear magnetic resonance imaging (MRI) machines, but can come from other electrical sources, such as from a faulty electro-cautery device.

When AC is passed through a medical electrode, it is usually intended for the AC to pass from say, an electrical medical device. However, AC passage can also be unintended, such as when a technician accidentally plugs the distal ends of an electrode into a wall outlet. For the most part, the passage of inductive current through a medical electrode is unintended, and often results from the wire leads of the electrode acting as a "pick up" for the inductive current. Both AC and inductive current can reach harmful levels which, when passed through a medical electrode, cause current densities which exceed the safety limit and result in tissue burns.

Figure 3:
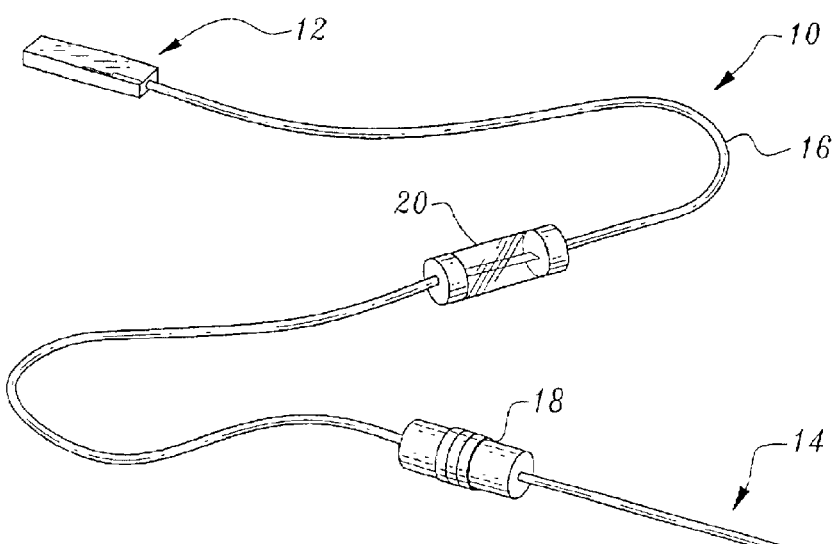
FIG. 3 is a perspective view of the inventive medical electrode, this embodiment being a needle electrode

The inventive medical electrode works to prevent harmful current, whether intended, or unintended, from passing to a patient, and causing tissue burns or electrocution. This can be accomplished by stopping the flow of current altogether, or through limiting the current to non-harmful levels. In FIG. 3, the inventive medical electrode 10 is shown, in the form of a needle electrode. Electrode 10 has a distal end 12, a proximal end 14, and a wire lead 16 extending between the proximal and distal ends, here shown in a partially coiled configuration. Wire lead 16 may be of various lengths capable of spanning the distance between a medical device to which the distal end 12 is removably attached, and the patient, upon whom the proximal end 14 is connected. Wire lead 16 can be comprised of insulated metallic wire such as 23–30 gage stainless steel or platinum wire, or another electrically conductive material. Distal end 12 is shown here as being a female connector, because present international standards require distal end to be a female connector, to avoid accidental plugging into AC wall outlets. Proximal end 14 is shown here as a needle which is inserted into the tissue of a patient. Usually a housing 18 is adjacent to proximal end 14, the housing 18 being used to manipulate proximal end 14 into a connection with the patient's tissue. While here distal end is a female connector and proximal end is a needle, the invention is not limited to this configuration and further non-limiting embodiments are discussed, below.

Continuing with FIG. 3, the inventive medical electrode 10 includes a current stoppage means 20 located thereon for preventing the passage of harmful current to the tissue of a patient. In FIG. 3, the preferred current stoppage means 20 is a fuse located in-line with the wire lead 16, about halfway down its length. A $\frac{1}{16}$ A (66 mA) "indicator" fuse manufactured by Littlefuse, Inc. located in-line upon the inventive medical electrode 10 has been found to adequately prevent the passage of harmful current to the tissue of a patient. This fuse would "blow" prior to harmful current reaching a patient's tissue. The configuration shown in FIG. 3 would adequately prevent the passage of harmful AC current should distal end 12 of electrode somehow be accidentally inserted into a wall outlet, for example.

Figure 4:
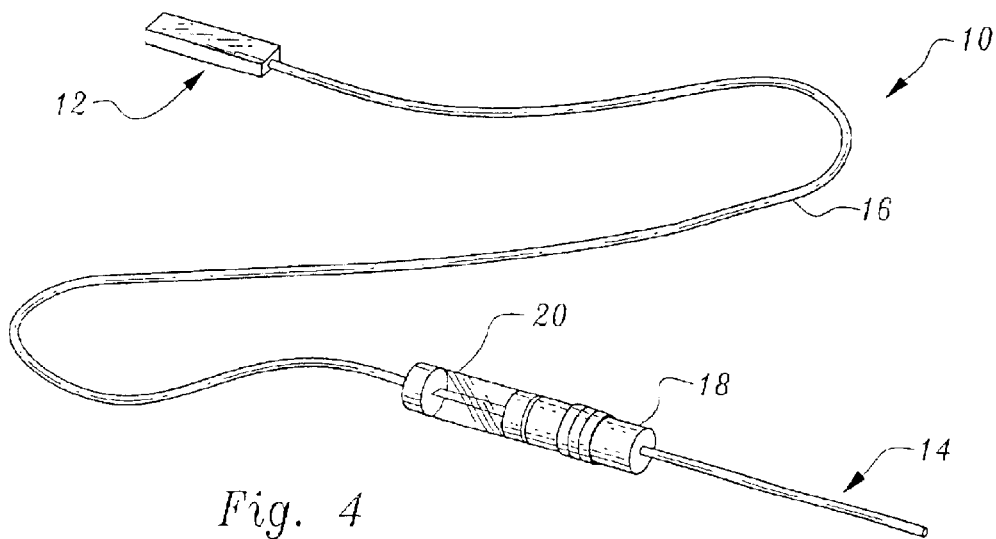
FIG. 4 is a perspective view of the inventive medical electrode, again showing a needle electrode style embodiment, this embodiment clearly showing the current stoppage means positioned aft of the wire lead.

For preventing the passage of both harmful AC current and harmful inductive current, the configuration shown in FIG. 4 is preferred. Here, current stoppage means 20 is placed aft of wire lead 16, and connected to proximal end 14 of electrode 10. Placement of current stoppage means 20 aft of wire lead 16 eliminates any portion of wire lead from becoming a conduit for the pick up and passage of harmful inductive current through to proximal end, and into a patient's tissue. In the prior embodiment 10 shown in FIG. 3, a portion of wire lead 16 was located aft of current stoppage means 20, which portion of wire lead 16 could still conceivably pick up harmful inductive current from an outside RF source, for example, and relay it to a patient's tissue, through proximal end 14.

Figure 5:
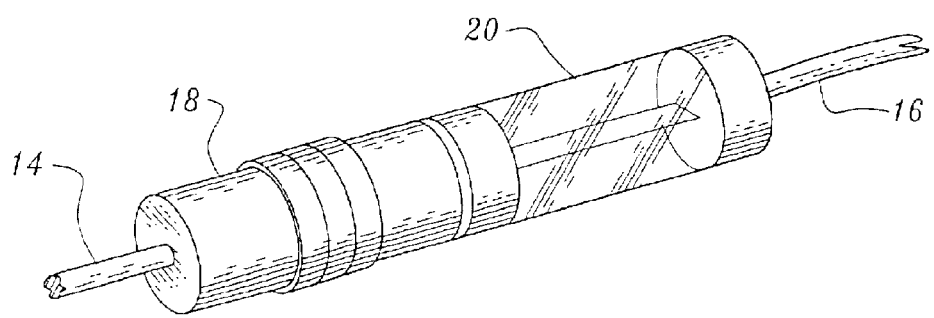
FIG. 5 is a close-up view of the proximal end of the inventive medical electrode, again showing a needle electrode style embodiment, this view also showing an indicator fuse serving as a current stoppage means.

FIG. 5 is a close-up view of an indicator fuse, which can act as a current stoppage means 20 for purposes of the invention. Indicator fuse 20 is positioned aft of wire lead 16 in the manner described for the embodiment of FIG. 4. An indicator fuse has been found to be useful in that upon burning out, a technician can readily view the burned out fuse and know that an electrode has been exposed to harmful current, and remedial measures can be taken to find the source of the harmful current for purposes of rendering the patient environment much safer.

Figure 6:
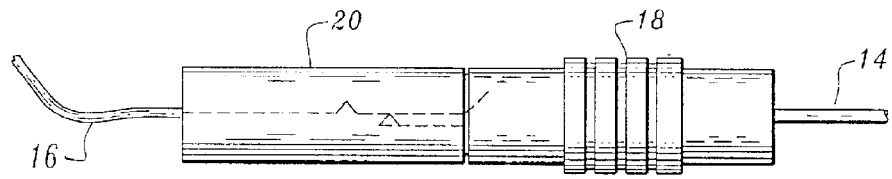
FIG. 6 is a close-up view of the proximal end of the inventive medical electrode showing a micro-circuit breaker as a current stoppage means.

FIG. 6 is a close-up view of a micro-circuit breaker acting as a current stoppage means 20. This configuration is especially useful because it allows expensive medical electrodes to be salvaged and used again by merely tripping the micro-circuit breaker 20, unlike most fuses which are typically destroyed (and the electrode with it) once they blow.

Figure 7:
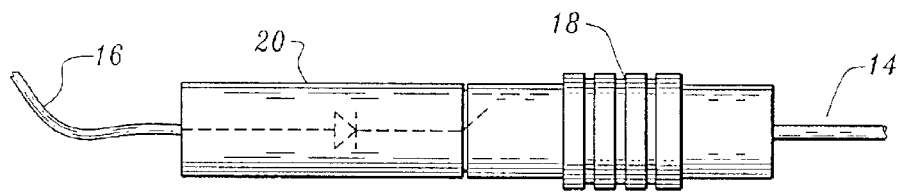
FIG. 7 is a close-up view of the proximal end of the inventive medical electrode showing a diode as a current stoppage means.

FIG. 7 is a close-up view of a diode acting as a current stoppage means 20. This diode 20 would severely restrict the passage of current, such that the current that was ultimately passed to a patient would not be harmful. This diode embodiment demonstrates that the inventive medical electrode 10 is not limited to current stoppage means which "stop" harmful current altogether, such as with fuses and micro-circuit breakers, but also includes current stoppage means which restrict or reduce harmful levels of current to levels which are not harmful. A diode which has been found to meet the needs of the invention by blocking current that exceeds 2 mA r.m.s/cm² is the MINI™ Diode manufactured by Littlefuse, Inc.

Figure 8:
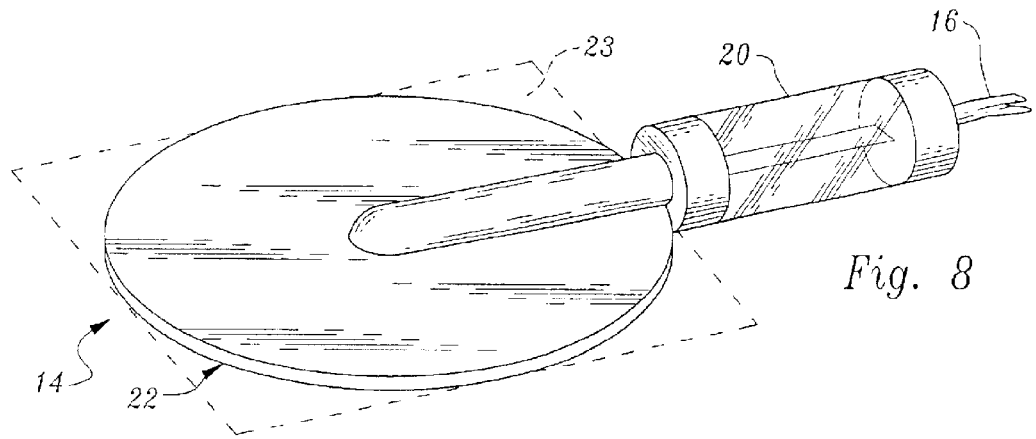
FIG. 8 is a close-up plan view of the inventive medical electrode, this embodiment being a plate electrode.
Figure 9:
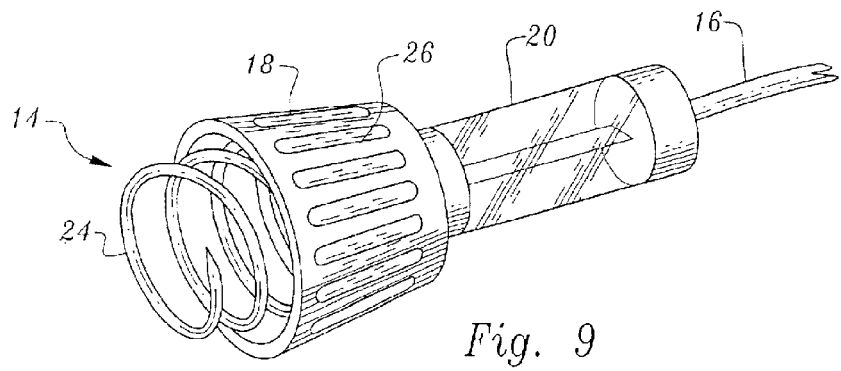
FIG. 9 is a close-up perspective view of the inventive medical electrode, this embodiment being a corkscrew electrode.

FIGS. 8–13 are various views of other types of the inventive medical electrode 10 intended to be exemplary and non-limiting. FIG. 8 is a plate electrode having an approximately flat proximal end 14, this end having an undersurface 22 for connecting to a patient. Here, the undersurface 22 is shown placed against a surface 23 (dotted lines), such as a patient's skin. Plate electrodes are typically disk shaped as shown, but can be rectangular, oval, oblong or even heart-shaped, to name a few additional configurations. In use, the undersurface 22 is typically adhered to a patient for monitoring purposes, such as in an EKG procedure. FIG. 9 is an electrode wherein the proximal end 14 is configured as a corkscrew 24, which is often used for monitoring during surgical procedures. The corkscrew 24 is designed for insertion into the tissue of a patient, and upon insertion, housing 18 has ridges 26 for gripping and turning, thereby turning corkscrew deeper into a patient's tissue, and insuring that the electrode will not fall out of a patient during a procedure. FIG. 10 is a strap electrode 10, shown wrapped around a patient's finger 27. FIG. 11 is an earplug electrode 10 which is inserted into a patient's ear canal 28. FIG. 12 is a clip electrode 10. FIG. 13 is a contact lens electrode 10 for an eye 29 application.

Figure 14:
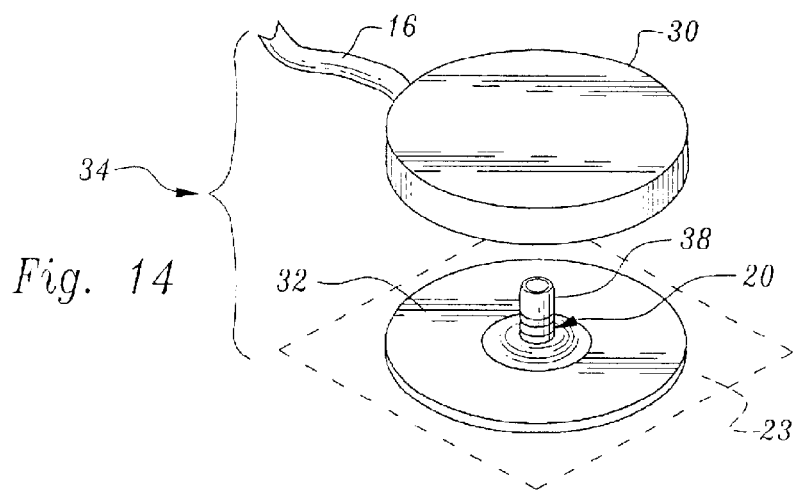
FIG. 14 is a close-up perspective view of the inventive medical electrode, this embodiment comprising two separable members.
Figure 15:
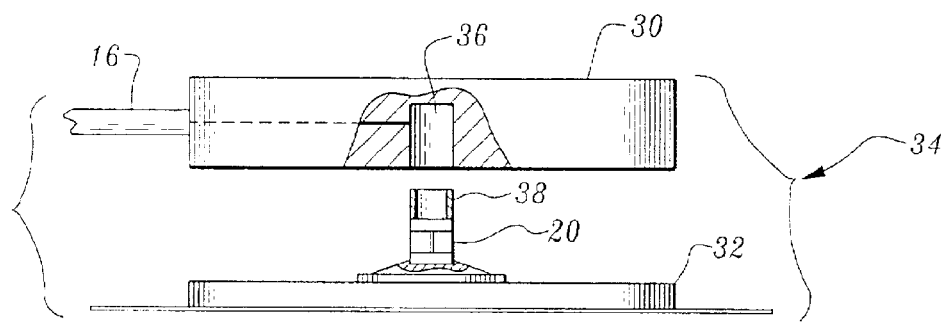
FIG. 15 is a side view of the embodiment shown in FIG. 14, here shown with the top and bottom members being separated.

FIGS. 14–15 show an electrode 10 having separable members. These types of electrodes generally comprise two separable members 30, 32 connectable by an electrical conducting means such as a snap 34 or connecting pin. FIG. 14 illustrates this embodiment of the inventive medical electrode as having a top member 30 and a bottom member 32. Top member 30 has a female portion 36 of snap 34, which is more visible in FIG. 15. Top member 30 would typically comprise a reusable portion of this embodiment of a safety electrode. Bottom member 32 is preferably disposable. Bottom member 32 is shown in FIG. 14 in its normal position for contacting a surface 23, such as a patient's skin. Current stoppage means 20 is preferably located beneath the male portion 38 of snap 34. Current stoppage means 20 is preferably comprised of a ¹⁄₁₆ A (66 mA) pico fuse #251 manufactured by Littlefuse, Inc. Male portion 38 of bottom member 32 snaps into female portion 36 of top member 30, with current stoppage means 20 creating a fusible link between the two members. In this configuration, fuse 20 of bottom member 32 will blow prior to harmful current reaching a patient's tissue.

Figure 16:
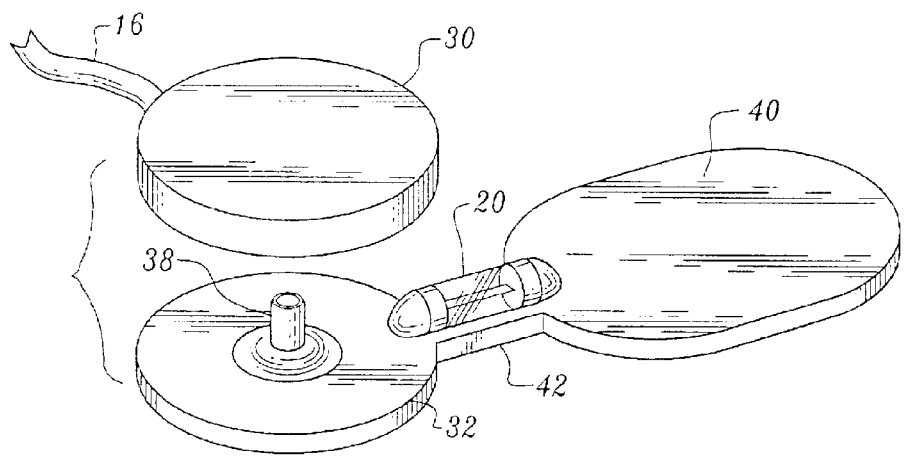
FIG. 16 is a close-up perspective view of the inventive medical electrode, this embodiment comprising two separable members.

Referring now to FIG. 16, an embodiment of the invention for a side snap electrode 10 is shown. Unlike the snap electrode of FIGS. 14–15, the side snap electrode has a pad 40 for contacting a patient's skin, with a bottom member 32 of snap 34 that is offset to the side of pad 40. An indicator fuse 20 forms a bridge 42 between snap portion 34 and pad 40, thereby creating a fusible link for preventing the passage of current from the snap portion 34 to the pad 40. Here, the indicator fuse 20 can be partially comprised of a heat sensitive dye contained within the fuse that turns color when the fusible link heats and blows. This configuration is preferred over the separable embodiment of FIGS. 14–15, if it is desirable to be able to see that the fuse has blown.

The inventive medical electrode described herein in various embodiments and equivalents solves a serious problem that has been overlooked by those skilled in the medical electrode arts. This problem is burning and electrocution caused by the passage of harmful current through an electrode to the tissue of a patient. Harmful current can be passed through an electrode whether it is plugged into an electrical medical device, or unplugged, as in the case of inductive current phenomena. Present methods, such as fusing electrical medical devices have proven wholly inadequate, as there are numerous cases of faulty fused machines still passing harmful current through to electrodes connected to such machines. The solution, as provided by the inventive medical electrode described herein has been to locate a current stoppage means such as a fuse, circuit breaker or diode upon the electrode itself. Also, to most thoroughly prevent any possibility of harmful current from induction, it is preferred that the current stoppage means be placed aft of the wire lead at the proximal end of the electrode. This preferred arrangement has proven to effectively prevent the passage of both harmful AC current from wall outlets and machine sources, as well as harmful inductive current picked up from RF sources in the medical environment.

Finally although the description above contains many specificities, these should not be construed as limiting the scope of the invention but as merely providing illustrations of some of the presently preferred embodiments of this invention. This invention may be altered and rearranged in numerous ways by one skilled in the art without departing from the coverage of any patent claims that are supported by this specification.

What is claimed is:

1. A medical electrode for preventing the passage of harmful current to a patient, the electrode comprising:

a distal end for connecting to a medical device;

a proximal end including a portion formed in the shaped shape of a contact lens for connecting to a patient;

a conductive lead connected between the distal and proximal ends; and a current stoppage means connected to the electrode at a location for preventing the passage of harmful current to the proximal end coupled to the proximal end of the electrode aft of the conductive lead.

2. A medical electrode for preventing the passage of harmful current to a patient, the electrode comprising:

a distal end for connecting to a medical device;

a proximal end for connecting to a patient;

a conductive lead connected between the distal and proximal ends; and a current stoppage means connected aft of the conductive lead and immediately adjacent to the proximal end of the electrode, wherein the current stoppage means is a circuit breaker.

3. A medical side-snap electrode for preventing the passage of harmful current to a patient, the electrode comprising:

a distal end for connecting to a medical device;

a proximal end for connecting to a patient;

a conductive lead connected between the distal and proximal ends; and a current stoppage means selected from the group consisting of a fuse or a circuit breaker, the current stoppage means coupled to the proximal end of the side-snap electrode aft of the conductive lead.

4. A medical electrode having separable members for preventing the passage of harmful current to a patient, the electrode comprising:

a distal end for connecting to a medical device;

a separable structure including top and bottom separable members, the separable structure being located at a proximal end of said electrode, the separable structure for connecting to a patient, the top member being positioned atop the bottom member, the bottom member comprising a pad for contacting a patient's skin, the pad located adjacent a connector portion, and a current stoppage means located between the pad and the connector portion.

5. The bottom member as recited in claim 4, wherein the current stoppage means is selected from the group consisting of a fuse, a diode or a circuit breaker.

6. The bottom member as recited in claim 4, wherein the current stoppage means is an indicator fuse.

7. The bottom member as recited in claim 4, wherein the connector portion further comprises a male connector.

* * * * *